United States Patent
Padmanabhan et al.

(10) Patent No.: US 8,518,328 B2
(45) Date of Patent: Aug. 27, 2013

(54) FLUID SENSING AND CONTROL IN A FLUIDIC ANALYZER

(75) Inventors: Aravind Padmanabhan, Plymouth, MN (US); Tom Rezachek, Cottage Grove, MN (US); Ron L. Bardell, St. Louis Park, MN (US)

(73) Assignee: Honeywell International Inc., Morristown, NJ (US)

( * ) Notice: Subject to any disclaimer, the term of this patent is extended or adjusted under 35 U.S.C. 154(b) by 1532 days.

(21) Appl. No.: 11/306,402

(22) Filed: Dec. 27, 2005

(65) Prior Publication Data

US 2007/0148039 A1    Jun. 28, 2007

(51) Int. Cl.
  *G01N 21/00*    (2006.01)

(52) U.S. Cl.
  USPC ......................................................... 422/67

(58) Field of Classification Search
  USPC ......................................................... 422/67
  See application file for complete search history.

(56) References Cited

U.S. PATENT DOCUMENTS

| | | | |
|---|---|---|---|
| RE28,801 E | 5/1976 | Acker et al. |
| 4,178,345 A | 12/1979 | Terk |
| 4,654,197 A | 3/1987 | Lilja et al. |
| 4,764,342 A | 8/1988 | Kelln et al. |
| 4,929,426 A | 5/1990 | Bodai et al. |
| 4,944,035 A * | 7/1990 | Aagardl et al. ............... 702/136 |
| 5,143,084 A | 9/1992 | Macemon et al. |
| 5,366,903 A | 11/1994 | Lundsgaard et al. |
| 5,405,510 A | 4/1995 | Betts et al. |
| 5,519,635 A | 5/1996 | Miyake et al. |
| 5,589,350 A | 12/1996 | Bochner |
| 5,905,518 A | 5/1999 | DeFilippis |
| 5,989,402 A * | 11/1999 | Chow et al. ................... 204/601 |
| 6,074,556 A | 6/2000 | Van Davelaar |
| 6,091,502 A | 7/2000 | Weigl et al. |
| 6,114,122 A | 9/2000 | Besemer et al. |
| 6,120,464 A | 9/2000 | Racchini et al. |
| 6,372,182 B1 | 4/2002 | Mauro et al. |
| 6,382,228 B1 | 5/2002 | Cabuz et al. |
| 6,488,896 B2 | 12/2002 | Weigl et al. |
| 6,549,275 B1 | 4/2003 | Cabuz et al. |
| 6,557,427 B2 | 5/2003 | Weigl et al. |
| 6,581,899 B2 | 6/2003 | Williams |
| 6,594,009 B2 | 7/2003 | Saccomanno |
| 6,597,438 B1 | 7/2003 | Cabuz et al. |
| 6,648,859 B2 | 11/2003 | Bitdinger et al. |
| 6,682,183 B2 | 1/2004 | Jones et al. |
| 6,700,130 B2 | 3/2004 | Fritz |

(Continued)

FOREIGN PATENT DOCUMENTS

WO    0173396    10/2001

*Primary Examiner* — Lore Jarrett

(74) *Attorney, Agent, or Firm* — Seager Tufte & Wickhem LLC

(57) ABSTRACT

Instrument-cartridge interfaces for fluidic analyzers that have an instrument and a removable cartridge are disclosed. For example, and in one illustrative embodiment, the instrument may include a needle that is adapted to penetrate a septum on a removable cartridge. In another illustrative embodiment, the instrument may include a plunger that is adapted to deform a deformable membrane on a removable cartridge. In yet another illustrative embodiment, the instrument may include a nozzle that is adapted to mate and seal with a flow channel on a removable cartridge. Techniques for detecting the flow rate in a flow channel on a removable cartridge, as well as the position of fluid in a flow channel of a removable cartridge, are also disclosed.

17 Claims, 14 Drawing Sheets

(56) References Cited

U.S. PATENT DOCUMENTS

| | | |
|---|---|---|
| 6,733,252 B2 | 5/2004 | Feygin et al. |
| 6,743,399 B1 | 6/2004 | Weigl et al. |
| 6,752,798 B2 | 6/2004 | McWethy et al. |
| 6,766,816 B2 | 7/2004 | Secondo |
| 6,773,100 B2 | 8/2004 | Kulpa et al. |
| 6,780,617 B2 | 8/2004 | Chen |
| 6,783,736 B1 | 8/2004 | Taylor et al. |
| 6,808,374 B2 | 10/2004 | Phallen |
| 6,852,284 B1 | 2/2005 | Holl et al. |
| 6,890,310 B2 | 5/2005 | Fracavilla et al. |
| 6,935,731 B2 | 8/2005 | Wirth et al. |
| 6,970,245 B2 | 11/2005 | Fritz et al. |
| 7,000,330 B2 | 2/2006 | Schwictenberg et al. |
| 7,004,929 B2 | 2/2006 | McWethy et al. |
| 7,016,022 B2 | 3/2006 | Fritz et al. |
| 7,061,595 B2 * | 6/2006 | Cabuz et al. .................. 356/72 |
| 2002/0190839 A1 * | 12/2002 | Padmanabhan et al. ........ 338/13 |
| 2005/0105077 A1 | 5/2005 | Padmanabhan et al. |
| 2005/0106066 A1 | 5/2005 | Saltsman et al. |
| 2005/0201903 A1 | 9/2005 | Weigl et al. |
| 2005/0205816 A1 | 9/2005 | Hayenga et al. |
| 2005/0243304 A1 | 11/2005 | Padmanabhan et al. |
| 2005/0255600 A1 | 11/2005 | Padmanabhan et al. |

* cited by examiner

FLUID SENSING AND CONTROL IN A FLUIDIC ANALYZER

FIELD

The present invention relates generally to fluidic analyzers, and more particularly, to fluidic analyzers that have an instrument-cartridge interface.

BACKGROUND

Chemical and/or biological analysis is important for life sciences research, clinical diagnostics and a wide range of environmental and process monitoring. In some cases, an analyzer is used to perform and/or assist in performing a chemical and/or biological analysis of a sample fluid. The sample fluid may be a liquid or a gas, depending on the application.

Some analyzers include an instrument that receives a removable, and in some cases, a disposable cartridge. In such analyzers, a sample fluid is often introduced or otherwise provided to the removable cartridge, and the instrument, through one or more interfaces, interacts with the removable cartridge to help perform and/or control the desired chemical and/or biological analysis. The interfaces may include, for example, fluid interfaces, electrical interfaces and/or other types of interfaces, depending on the application. The integrity of the interfaces is often important to the functioning of the overall device. For example, fluid interfaces often convey one or more fluids (either liquid or gas fluids) between the removable cartridge and the instrument, and/or visa-versa, and it is often desirable for the fluid interfaces to be substantially leak-free, reliable and cost effective.

SUMMARY

The following summary of the invention is provided to facilitate an understanding of some of the innovative features unique to the present invention and is not intended to be a full description. A full appreciation of the invention can be gained by taking the entire specification, claims, drawings, and abstract as a whole.

The present invention relates generally to fluidic analyzers, and more particularly, to fluidic analyzers that have one or more instrument-cartridge interfaces. In some embodiments, the fluidic analyzer may be a flow cytometer and/or hematology analyzer having one or more leak-free interfaces between an instrument and a disposable cartridge, but other fluidic analyzers may be used as well.

In one illustrative embodiment, a fluidic analyzer is provided that includes a cartridge that has a first flow channel defined by flow channel walls, and an opening that extends from outside of the cartridge and into the first flow channel. A septum is disposed in or over the opening and is secured to at least a portion of the cartridge with a fluid tight seal. An instrument is also provided for receiving the cartridge. A first needle may be attached to the instrument. The first needle may be sized to fit in the opening of the first flow channel of the cartridge, and pierce through the septum. With the first needle situated in the opening of the first flow channel and through the septum, the instrument may induce a flow in the first needle, which in turn, induces a flow in the first flow channel of the cartridge. In some cases, the instrument may include a sensor or the like to sense the flow induced in the first needle. The flow induced in the first needle may be related to the flow induced in the first flow channel of the cartridge.

The septum may be adapted to provide a relatively fluid tight seal around the first needle when the first needle pierces and extends through the septum. Alternatively, or in addition, the septum may be adapted to reseal the opening after withdrawal of the first needle from the septum.

In some cases, the first needle may include a body, a tip, and a stopping mechanism. The stopping mechanism may be disposed around at least part of the body of the first needle and offset back from the tip of the first needle by a distance. The stopping mechanism may be offset by a distance that allows the tip of the first needle to pierce through the septum, but prevents the tip of the first needle from engaging a back side of the first flow channel of the cartridge.

In some embodiments, the cartridge includes a second flow channel, and the instrument includes a second needle that passes fluid between the second flow channel of the cartridge and the instrument. In some cases, the second needle is in fluid communication with the first needle via a fluid pathway of the instrument. The instrument may include a flow sensor for sensing the fluid flow in the fluid pathway of the instrument, if desired. In other cases, the second needle may provide an independently controlled pressure to the cartridge. In some embodiments, the cartridge may include the first and/or second needle, and the instrument may include one or more corresponding septums, as desired.

In another illustrative embodiment, a fluidic analyzer is provided that includes a cartridge with a flow channel defined by flow channel walls, and an opening that extends from outside of the cartridge and into the flow channel. A resilient and/or flexible membrane may be disposed in or over the opening and secured to at least a portion of the cartridge via a fluid tight seal. The fluid analyzer may further include an instrument for receiving the cartridge. The instrument may have a plunger that is in registration with the resilient and/or flexible membrane of the cartridge when the cartridge is received by the instrument. The instrument may further have a moving mechanism that moves at least an end of the plunger into engagement with the resilient and/or flexible membrane of the cartridge so as to deform the resilient and/or flexible membrane, which changes the volume of a fluid chamber on the cartridge, which in turn, induces a flow in the flow channel of the cartridge.

The plunger may be any type of plunger. For example, the plunger may include a rigid end, and the moving mechanism of the instrument may move the rigid end of the plunger toward the resilient and/or flexible membrane to deform the resilient and/or flexible membrane. Alternatively, the plunger may include a deformable resilient and/or flexible membrane, and the moving mechanism of the instrument may include a pressure source that creates a pressure behind the resilient and/or flexible membrane of the plunger end to deform the resilient and/or flexible membrane of the plunger end toward the resilient and/or flexible membrane of the cartridge. This, in turn, deforms the resilient and/or flexible membrane of the cartridge, and ultimately, induces a flow in the flow channel of the cartridge.

In another illustrative embodiment, a fluidic analyzer is provided that includes a cartridge that has a first major surface and an opposing second major surface, with a flow channel positioned between the first major surface and the second major surface. The cartridge may further have an opening extending through the first major surface and into the first flow channel. The fluidic cartridge may further have an instrument for receiving the cartridge. The instrument may have a pressure source that is at least selectively in fluid communication with a nozzle. The pressure source may be any type of pressure source that produces either positive or negative pressure. The nozzle is positioned over the opening in the cartridge and forms a substantially fluid tight seal therewith when the cartridge is received by the instrument. The instrument may control the pressure of the pressure source so that a desired flow is induced in the flow channel of the cartridge via the nozzle/opening interface. In some embodiments, the cartridge may include a one-way valve in the opening or the flow channel, which may help prevent fluid from exiting the cartridge when the cartridge is removed from the instrument.

In yet another illustrative embodiment, a fluidic cartridge is provided that has a cartridge with a chamber defined by one or more chamber walls. The fluidic cartridge may further have an instrument that receives the cartridge. The instrument may have a force mechanism for applying a force to the cartridge that deforms at least part of one or more of the chamber walls to induce a flow in the cartridge. In some cases, the at least part of the one or more chamber walls that is deformed includes a flexible membrane that deforms under the applied force, thereby changing the volume of the chamber and inducing a flow in a fluid channel of the cartridge. In other cases, the at least part of the one or more chamber walls that is deformed is a relatively rigid wall that collapses under the applied force, thereby changing the volume of the chamber of the cartridge. The force mechanism may be any type of force mechanism. For example, the force mechanism may include a roller that when rolled along the cartridge, at least part of one or more of the chamber walls is deformed (e.g. compressed) by the roller to induce a flow in the cartridge.

In another illustrative embodiment, a fluidic cartridge is provided that includes a disposable cartridge that has a flow channel for transporting a fluid down the flow channel, wherein the fluid has one or more detectable characteristics. The fluidic cartridge also includes an instrument for receiving the disposable cartridge. The instrument may have a first detector situated at a first location along the flow channel for detecting at least one of the one or more detectable characteristics of the fluid. The instrument may use the detection of the one or more detectable characteristics of the fluid by the first detector to determine a measure of flow rate of the fluid in the flow channel of the cartridge and/or a current position of the fluid in the flow channel. The instrument may further have a second detector, positioned at a second location along the flow channel spaced downstream of the first location, for detecting at least one of the one or more detectable characteristics of the fluid. The instrument may use the detection of the one or more detectable characteristics of the fluid by the first detector and the second detector to determine a measure of flow rate of the fluid in the flow channel and/or a current position of the fluid in the flow channel. The fluid that is detected may be a sample fluid of interest, a pusher fluid for pushing a sample fluid of interest along the flow channel, or any other fluid as desired.

BRIEF DESCRIPTION

Figure 13:
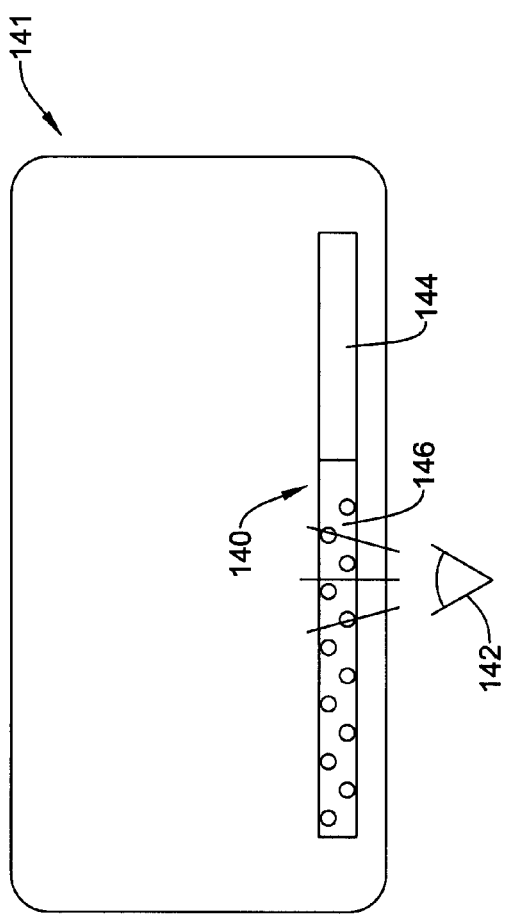
Figure 14A:
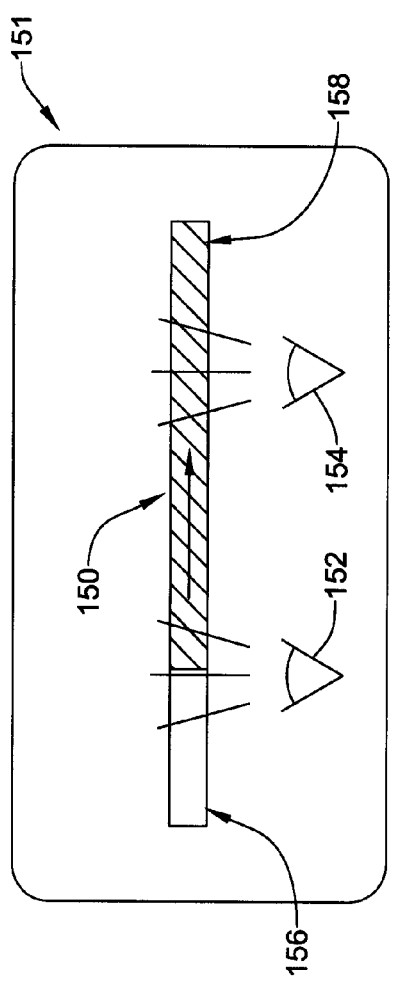
Figure 14B:
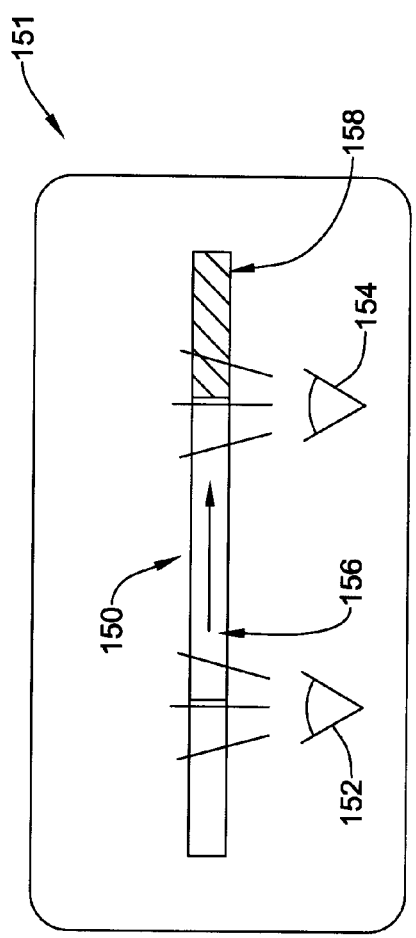

FIG. 13 is a schematic view of an illustrative fluidic analyzer that includes an instrument with a detector for determining the flow rate and/or current position of a fluid in a flow channel of a cartridge; and FIGS. 14A-14B are schematic views of an illustrative fluidic analyzer that includes an instrument with two (or more) detectors for determining the flow rate and/or current position of a fluid in a flow channel of a cartridge.

DETAILED DESCRIPTION

The following description should be read with reference to the drawings wherein like reference numerals indicate like elements throughout the several views. The detailed description and drawings show several embodiments which are meant to be illustrative of the claimed invention.

The present invention relates generally to fluidic analyzers, and more particularly, to fluidic analyzers that have one or more fluidic instrument-cartridge interfaces. In some embodiments, the fluidic analyzer may be a flow cytometer, a hematology analyzer, a clinical chemistry analyzer (e.g. glucose analyzer, ion analyzer, electrolytes analyzer, dissolved gasses analyzer, etc.), a urine analysis analyzer or any other suitable analyzer having one or more leak-free interfaces between an instrument and a disposable cartridge.

Figure 1:
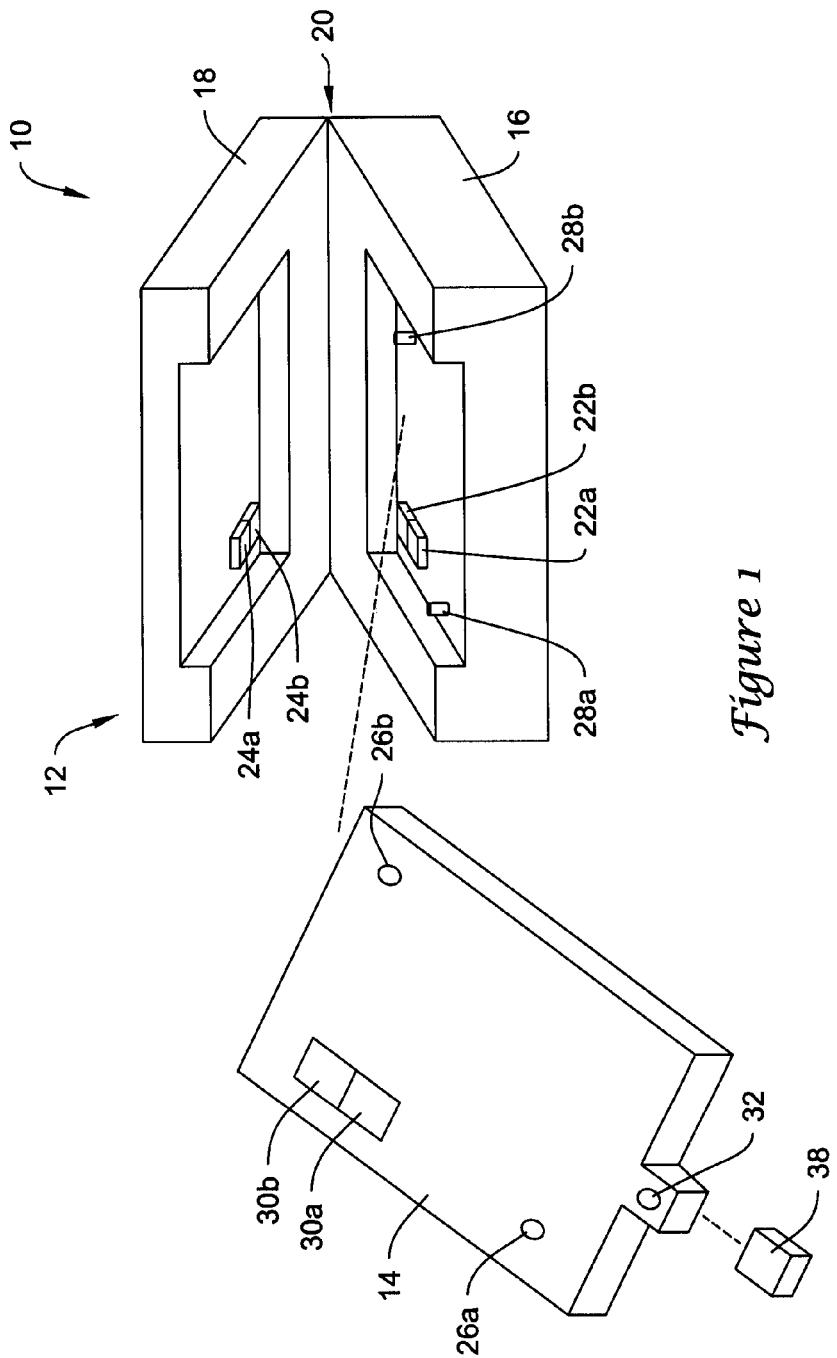
FIG. 1 is a perspective view of an illustrative portable cytometer.

FIG. 1 is a perspective view of an illustrative portable cytometer. The illustrative cytometer 10 includes an instrument 12 and a removable, and in some cases, disposable cartridge 14. The illustrative instrument 12 includes a base 16, a cover 18, and a hinge 20 that attaches the base 16 to the cover 18. The base 16 may include light sources 22a and 22b, along with associated optics and the necessary electronics for operation of the cytometer. The cover 12 may include light detectors 24a and 24b with associated optics.

The removable cartridge 14 may receive a sample fluid, such as, for example, a blood sample, via a sample collector port 32. A cap 38 may be used to protect the sample collector port 32 when the removable cartridge 14 is not in use. The removable cartridge 14 may perform blood dilution, red cell lysing, and hydrodynamic focusing for core formation. The removable cartridge 14 may be constructed similar to the fluidic circuits available from Micronics Technologies, some of which are fabricated using a laminated structure with etched channels.

During use, the removable cartridge 14 is inserted into the instrument when the cover 18 is in the open position. The removable cartridge 14 may include holes 26a and 26b for receiving registration pins 28a and 28b in the base 16, which may help provide alignment and coupling between the different parts. The removable cartridge 14 also may includes transparent flow stream windows 30a and 30b, which are in alignment with the arrays of the light sources 22a and 22b, and light detectors 24a and 24b.

To initiate a test, the cover 18 may be lifted and a new cartridge 14 may be placed and registered onto the base 16. A sample fluid is introduced into the sample collector 32. The cover 18 is then closed. In some cases, the removable cartridge 14 provides blood dilution, red cell lysing, and hydrodynamic focusing for core formation. In some cases, the instrument 12 performs a white blood cell cytometry measurement. For example, the light sources 22a and 22b, light detectors 24a and 24b and associated control and processing electronics may perform differentiation and counting of white blood cells based on light scattering and/or fluorescent signals. Rather than using a hinged construction for the housing 12, it is contemplated that a sliding cartridge slot or any other suitable construction may be used, as desired.

To perform such an analysis, the sample fluid (e.g. blood sample) may need to be pushed (or pulled) through one or more flow channels of the cartridge 14. Reagents and/or other fluids may also need to be pushed (or pulled) through one or more flow channels. In some cases, the instrument 12 may aid in creating the necessary flows in the cartridge though one or more instrument/cartridge interfaces. Alternatively, or in addition, the instrument 12 may be used to monitor and/or control the flows on the cartridge.

Figure 2:
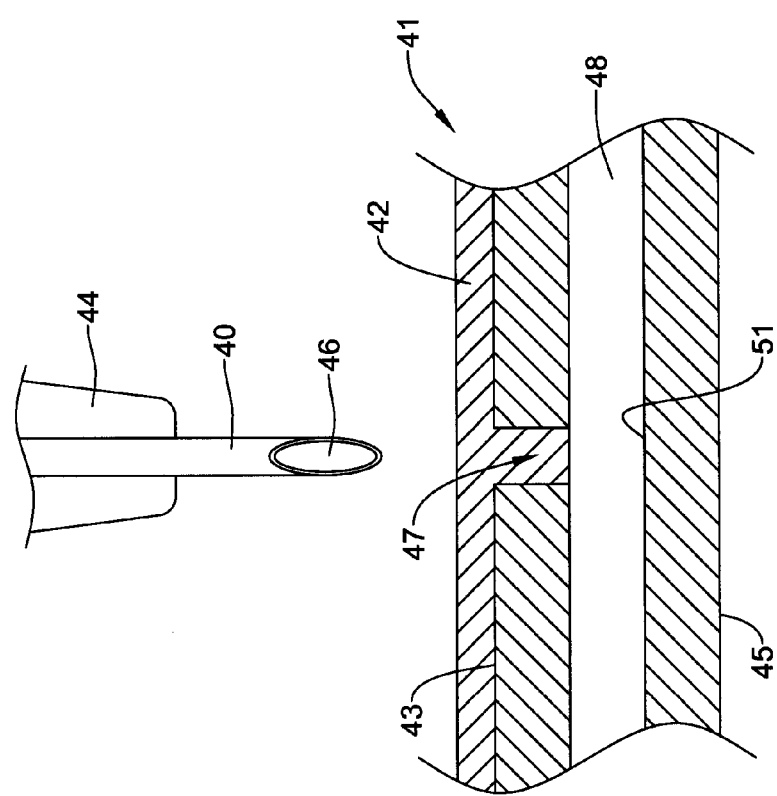
FIG. 2 is a schematic partial cross-sectional side view of an illustrative fluidic analyzer that includes a needle in an instrument/cartridge interface.

FIG. 2 is a schematic partial cross-sectional side view of an illustrative fluidic analyzer that includes a needle in an instrument/cartridge interface. In the illustrative embodiment, a cartridge 41 is shown as having a flow channel 48, defined by flow channel walls. The flow channel 48 is provided between an upper major surface 43 and a lower major surface 45 of the cartridge 41. In some cases, the flow channel 48 may be a long, thin flow channel in the cartridge 41. However, it is contemplated that the flow channel 48 may take on any suitable size or shape, as desired. In the illustrative embodiment, an opening 47 is provided between the flow channel 48 and the upper major surface 43.

A septum 42 is disposed in or over the opening 47 to form a fluid tight seal. In some cases, the septum 42 also extends over all or a portion of the upper major surface 43 of the cartridge 41 as shown, but this is not required. The septum 42 may prevent or substantially prevent fluid from flowing through the opening 47 in the flow channel 48 and out of the cartridge 41.

The septum 42 may be adapted to allow an object, such as a needle 40 or any other suitable object, to pierce the septum 42 and become in fluid communication with the flow channel 48. The septum 42 may also form a seal around the needle 40 to prevent or substantially prevent fluid from passing between the outside of the needle 40 and the septum 42. The septum 42 may also be adapted to reseal the opening created by the needle 40 after the needle 40 is removed from the septum 42. In some cases, as the needle 40 is withdrawn, the septum 42 may also wipe the needle 40 to help remove residual fluid from the needle 40. The septum 42 may be made from, for example, a resilient and/or flexible material such as an elastomer (e.g. rubber) or the like.

In the illustrative embodiment, the needle 40 has an elongated-tubular body with a hollow core to allow fluid to flow therethrough. The body may be attached at one end to an instrument. The other end of the needle 40 may terminate in a tip 46, which may be adapted for insertion into the cartridge 41 through the septum 42. In the illustrative embodiment, the tip includes a tapered pointed tip that may allow the needle to more easily pierce the septum 42 without coring the septum 42. However, it is contemplated that any suitable needle 40 tip may be used, as desired.

In some embodiments, the needle 40 may also have a stopping mechanism 44 disposed around and secured relative to the body of the needle 40. The stopping mechanism 44 may extend laterally outward from the body by a distance, and may be offset by an offset distance from the tip 46 of the needle 40. The stopping mechanism 44 may assist in inserting the needle 40 to a consistent and proper depth. In the illustrative embodiment, the needle 40 may pierce the septum 42 and may move down until the tip 46 of the needle is in fluid communication with the flow channel 48 and the stopping mechanism 44 engages the top surface of the septum 42 (or cartridge 41). With the needle 40 fully inserted, the offset distance of the stopping mechanism may be set to help ensure that the tip 46 of the needle 40 does not engage the back side wall 51 of the flow channel 48, when this is desired. Thus, in some illustrative embodiments, the stopping mechanism 44 may help prevent over and under insertion of the needle 40 into the cartridge.

When inserted, the hollow opening of the needle 40 tip 46 may be used to transfer a fluid and/or a pressure between the instrument (see FIG. 1) and the flow channel 48 of the cartridge 41. In some cases, the instrument may provide a fluid and/or a pressure that creates a desired flow in the flow channel 48 of the cartridge 41.

For example, and in some cases, the instrument may have a reservoir of fluid thereon. The fluid may be, for example, a reagent fluid, a lyse fluid, a sheath fluid, a pusher fluid, or any other suitable fluid, as desired. The fluid from the instrument may be provided to the flow channel 48 of the cartridge 41 through the needle 40, and create a flow of fluid in the flow channel 48. In some cases, by knowing the flow rate at which the fluid leaves the instrument, the flow in the flow channel 48 may be determined and/or controlled.

It is contemplated that the cartridge 41 may be removable or even disposable. The removable cartridge 41 may, in some embodiments, be inserted into an instrument that is adapted to receive the cartridge 41. The instrument may include, for example, a base, a cover and a needle 41. Once inserted, the cover of the instrument may be closed. In some cases, the needle 40 of the instrument may already be sufficiently aligned with the septum, while in other cases, the needle 40 may need to be aligned. Once aligned, the needle 40 may be actuated toward the cartridge 41 and may pierce the septum 42 and move to a position with the tip 46 of the needle 40 in fluid communication with the flow channel 48 of the cartridge 41. In some cases, the actuation or movement of the needle 40 may be automated, such as by a motor or the like, which actuates the needle 40 between an inserted position and a withdrawn position. A controller may be used to control the motor. Alternatively, it is contemplated that the needle 40 may be moved into position manually, such as by manually inserting and withdrawing the needle 40 from the cartridge 41.

Once the needle 40 is inserted into the cartridge 41 with the opening of the tip 46 positioned in the flow channel 48 of the cartridge 41, a fluid may be delivered from the instrument to the flow channel 48 of the cartridge 41 at a controlled flow rate. The fluid may be a gas or a liquid fluid, as desired. In the automated process, the flow rate may also be controlled by the controller, if desired.

After the needle 40 and instrument deliver the desired fluid to the cartridge 41, the needle 40 may be withdrawn so that the cartridge 41 can be removed from the instrument and, in some cases, properly disposed of. Again, the withdrawal of the needle 40 may be automated or manual performed as desired. In some cases, as the needle 40 is withdrawn from the cartridge 41, residual fluid is wiped off the needle 40 by the septum 42.

In some cases, the fluid flow rate provided by the instrument along with its correlation to the flow rate of the sample in the cartridge 41 can be determined. This may provide a relatively easy way to accurately determine and/or control the flow rate of the sample fluid in the flow channel 48 of the cartridge 41.

Prior to a measurement, it is contemplated that the instrument may flush the body and tip 46 of the needle 40 with a fluid before the needle 40 is inserted into the cartridge 41. This may help remove a possible contamination source from one cartridge to another. At the end of a measurement, the outside of the needle 40 body and tip 46 may be wiped off by the septum 42 during withdrawal, also helping to remove a possible contamination source. Also, the small scale or small surface area of the tip 46 of the needle 40 may help reduce the quantity of sample fluid that may be a source of contamination.

In some cases, a heat sterilization process may be introduced to sterilize the tip 46 of the needle 40 between cartridge measurements. For example, the sterilization process may be a rapid heat and cool cycle similar to that of a heat transfer pin. This process, in some cases, may be provided after each use of the needle 40, as desired. In addition, a one way valve may be provided in the instrument and/or cartridge 41, which may help prevent backflow of fluids into the instrument and/or cartridge 41. This may be particularly useful during a period of power loss.

Figure 3:
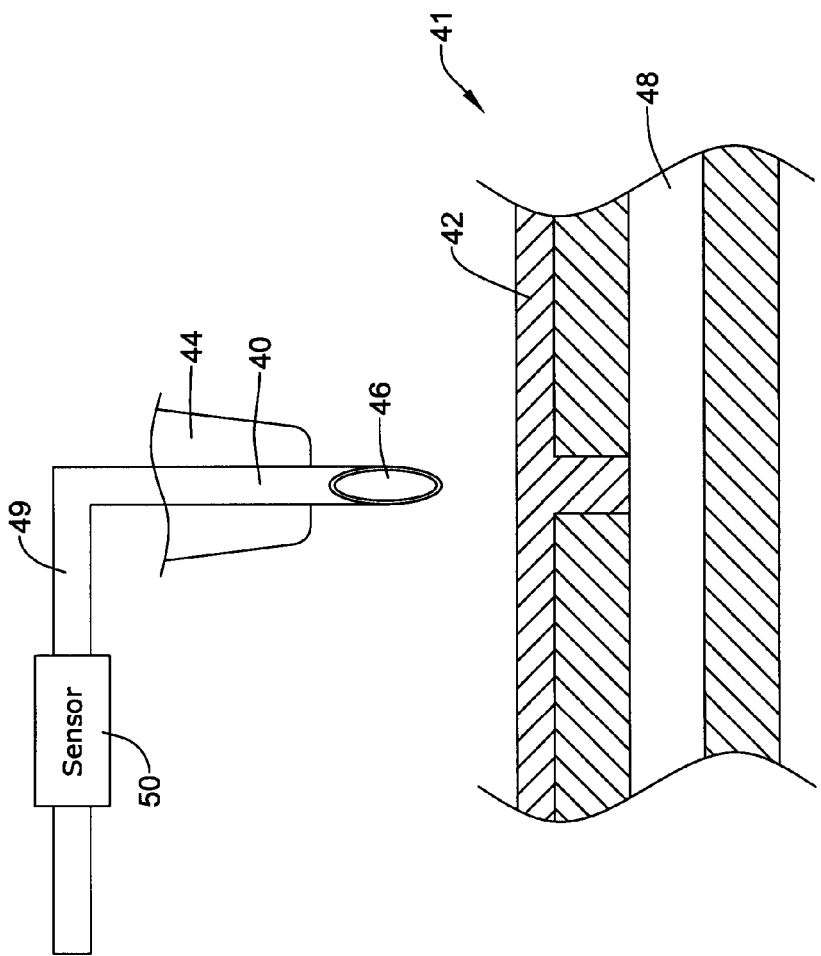
FIG. 3 is a schematic partial cross-sectional side view of the illustrative embodiment of FIG. 2 with a flow sensor in line with the needle.

FIG. 3 is a schematic partial cross-sectional side view of the illustrative embodiment of FIG. 2 with a sensor 50 placed in line with the needle 40. As illustrated, the sensor 50 senses a characteristic of the fluid in a supply flow channel 49 of the instrument. The sensor 50 may measure, for example, the flow rate, pressure or other characteristic of the fluid while the fluid is still in the instrument or, in other words, before the fluid leaves the instrument through the needle 40. In one illustrative embodiment, the sensor 50 may be a thermal anemometer type flow sensor such as described in, for example, U.S. Pat. Nos. 4,478,076, 4,478,077, 4,501,144, 4,651,564, 4,683,159, and 5,050,429, all of which are incorporated herein by reference. However, it is contemplated that the sensor 50 may be any suitable type of flow sensor, as desired.

By positioning the sensor 50 adjacent the flow channel 49 in the instrument, the sensor 50 may be able to directly measure the flow rate of the fluid passing through the needle 40. By knowing the flow rate passing through the needle 40, the flow rate in the flow channel 48 of the cartridge may also be determined. Alternatively, or in addition, the sensor 50 may be used to detect one or more characteristics of the fluid, such as thermal conductivity, specific heat, fluid density, electrical resistivity, and/or other characteristics of the fluid to, for example, help identify or verify that the fluid passing through the flow channel 49 is the expected fluid or expected fluid type. This may help verify that the expected fluid is actually being used in the flow channel 48 during a particular analysis or procedure.

The sensor 50 may be coupled to a controller (not shown) of the instrument. The controller may send as signal to activate the sensor 50 and may send a signal to deactivate the sensor 50, as desired. In return, the sensor 50 may provide data about the flow rate or other characteristic of the fluid passing through flow channel 49, as desired, to the controller. Alternatively, or in addition, the sensor 50 may be positioned on the cartridge 41, and may be used to, for example, directly measure the flow rate in the flow channel 48 of the cartridge 41. However, this may increase the cost of the cartridge 41.

Figure 4:
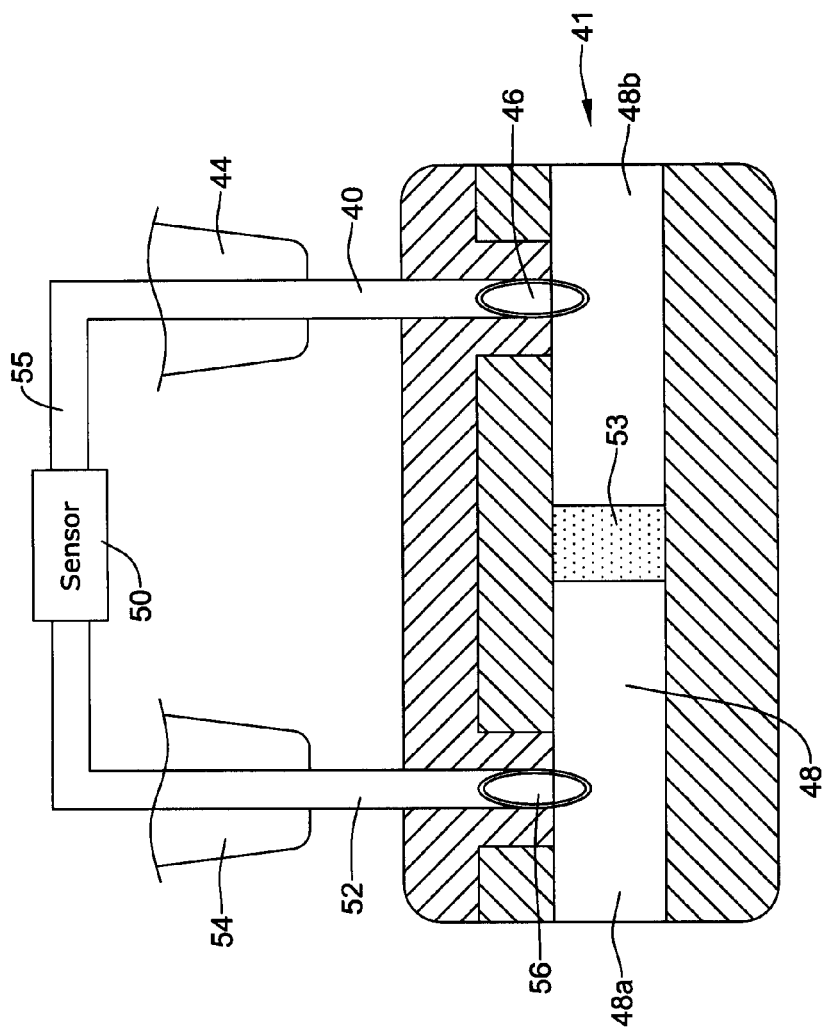
FIG. 4 is a schematic view of another illustrative fluidic analyzer that includes two (or more) needles in the instrument/cartridge interface.

FIG. 4 is a schematic view of another illustrative fluidic analyzer that includes two (or more) needles 40 and 52 in the instrument/cartridge interface. In one illustrative embodiment, the cartridge 41 includes a first flow channel 48a and a second flow channel 48b. The first flow channel 48a and the second flow channel 48b are separated by a wall 53, indicated in a dotted crosshatch in FIG. 4. The first needle 40 may, for example, extract a fluid from the first flow channel 48a of the cartridge 41, and the second needle 52 may return the fluid back to the second flow channel 48b of the cartridge 41. The instrument may have a flow channel 55 that fluidly connects the first needle 40 and the second needle 52. A flow sensor 50 may be provided in line with the flow channel 55 of the instrument, and may provide a measure of the flow rate in the first flow channel 48a and/or the second flow channel 48b of the cartridge. By moving the flow sensor 50 to the instrument, rather than providing the flow sensor 50 on the cartridge 41, the cost of the cartridge 41 may be reduced. Alternatively, or in addition, the flow sensor 50 may be used to detect one or more characteristics of the fluid, such as thermal conductivity, specific heat, fluid density, electrical resistivity, and/or other characteristics of the fluid to, for example, help identify or verify that the fluid passing through the first flow channel 48a and/or the second flow channel 48b of the cartridge is the expected fluid. This may help verify that the expected fluid is actually being used in the first flow channel 48a and/or the second flow channel 48b during a particular analysis or procedure.

During use, the first needle 40 and the second needle 52 may be inserted simultaneously or sequentially into the cartridge 41 through their respective septums. Such insertion may be similar to that described above with reference to FIG. 2. Once both of the needles 40 and 52 are inserted into the cartridge 41, the first needle 40 may extract the fluid from the flow channel 48a in the cartridge 41 and cause it to flow through the "off card" flow channel 55. When in the "off card" flow channel 55, the sensor 50 may measure the flow rate (and/or other characteristics) of the fluid. After the flow rate is measured, the fluid may pass to the second needle 52, where it is returned to flow channel 48b of the cartridge 41. After the cartridge 41 is used, both needles 40 and 52 may be withdrawn from the cartridge 41, again similar to that described above with reference to FIG. 2.

In another illustrative embodiment, the wall 53, indicated in dotted crosshatch in FIG. 4, may not be present. That is, both the first needle 40 and the second needle 52 may access a common flow channel labeled 48. The second needle 52 may be positioned either upstream or downstream of the first needle 40. In this configuration, the first needle 40 may transmit a first pressure to the sensor 50, and the second needle 52 may transmit a second pressure to sensor 50. The sensor may be, for example, a differential pressure sensor. From the difference in pressure sensed at the two locations along the flow channel 48, the flow rate along the flow channel 48 may be determined. A restriction may be positioned in the flow channel 48 between the first needle 40 and the second needle 52 to increase the pressure drop therebetween, if desired. It is contemplated that the needles discussed above may be provided on a removable cartridge, and the corresponding septums may be placed on the instrument, if desired.

Figure 5:
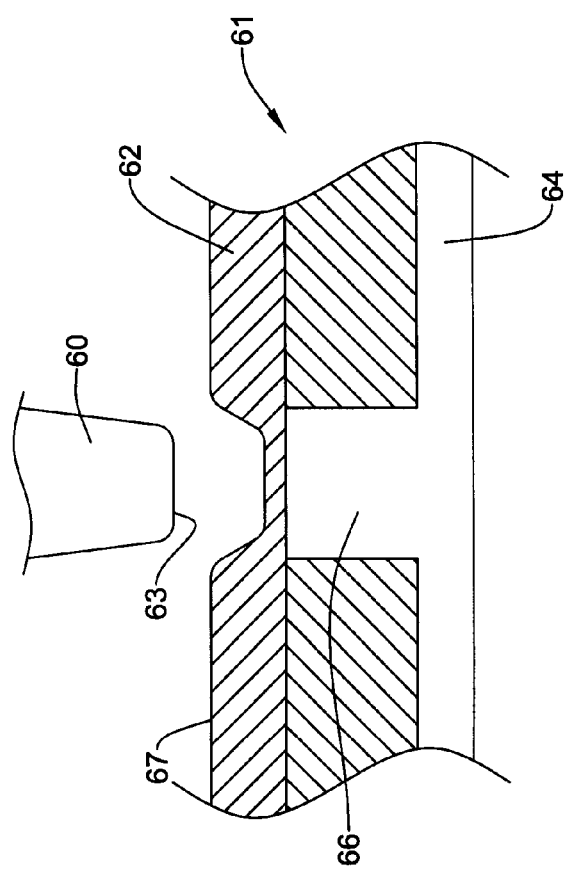
FIG. 5 is a schematic partial cross-sectional side view of another illustrative instrument/cartridge interface.

FIG. 5 is a schematic partial cross-sectional side view of another illustrative instrument/cartridge interface. In the illustrative embodiment, the instrument may include a plunger 60 with a relatively rigid end 63. The plunger may be, for example, a screw, a piston, or any other suitable device, as desired. In the case of a screw type plunger, it is contemplated that the screw may be a fine-pitch screw. However any suitable screw be used, as desired.

In the illustrative embodiment, the plunger 60 is attached or part of an instrument, and may be actuated up and down by an actuator. In some cases, the actuator may be controlled by an automated process. In such cases, the instrument may include a motor (not shown), such as a micro stepper motor, to control the position of the plunger 60. Alternatively, it is contemplated that under some circumstances, the actuation of the plunger 60 may be provided manually, such as, for example, by a lever, pressure button, or any other manual method, as desired.

In the illustrative embodiment, a removable cartridge 61 may have a fluid storage cavity 66 defined by storage cavity 66 walls, in which, a fluid may be stored. In one case, the fluid storage cavity 66 may be a cylindrical shaped storage cavity 66 having a relatively larger radius than height so as to fit on a relatively thin disposable cartridge. However, it is contemplated that the storage cavity 66 may be any suitable size or shaped as desired. The illustrative storage cavity 66 is fluidly coupled to a flow channel 64 on the cartridge 61.

At least a portion of one or more of the walls of the storage cavity 66, in most cases, an external wall of the cartridge 61, may include a membrane 62. In some cases, the membrane 62 may be a resilient and/or flexible membrane, such as an elastomeric membrane. In some cases, the membrane 62 may be provided by first removing a portion of the cartridge 61 to define an opening forming the storage cavity 66. Then, the membrane 62 may be disposed in and/or over the opening and, in some cases, over a portion of the upper surface of the cartridge 61 to form a fluid tight seal.

The size of the opening may be larger than the end 63 of the plunger 60, thus, allowing the plunger 60 to deform and displace the membrane 62 into the storage cavity 66. In some cases, the portion of the membrane 62 that is disposed over the opening may be recessed from the upper surface 67 of the cartridge 61. Such a recessed membrane 62 may help prevent accidental compression or displacement of the membrane 62, which could lead to accidentally inducing a flow in the flow channel 64 of the cartridge 61.

The illustrative embodiment may induce a flow of fluid in the flow channel 64 of the cartridge 61 by moving the plunger 60 against the membrane 62, deforming and displacing the membrane 62 toward the storage cavity 66, which in turn, displaces the fluid stored in the storage cavity 66 down the flow channel 64.

During use, the cartridge 61 may first be positioned in an instrument. In some cases, the instrument may align the plunger 60 with the storage cavity 66 of the cartridge 61. Next, the instrument may move the plunger 60 in contact with the membrane 62, but not yet displacing the membrane 62. The instrument may then drive the plunger 60 into the membrane 62, displacing the membrane 62 into the storage cavity 66, and inducing a flow in the flow channel 64 of the cartridge. The instrument may then withdraw the plunger 60. In some cases, the plunger 60 may be actuated in a pulsing manner or a steady manner. More generally, it is contemplated that the instrument may move the plunger 60 at a rate profile that induces a desired flow rate in the flow channel 64 of the cartridge 61. In the illustrative embodiment, the membrane 62 may help serve as a physical barrier between the instrument and the fluid in the cartridge 61. Having this barrier can reduce the risk of contamination of the cartridge 61 and/or the instrument.

Figure 6:
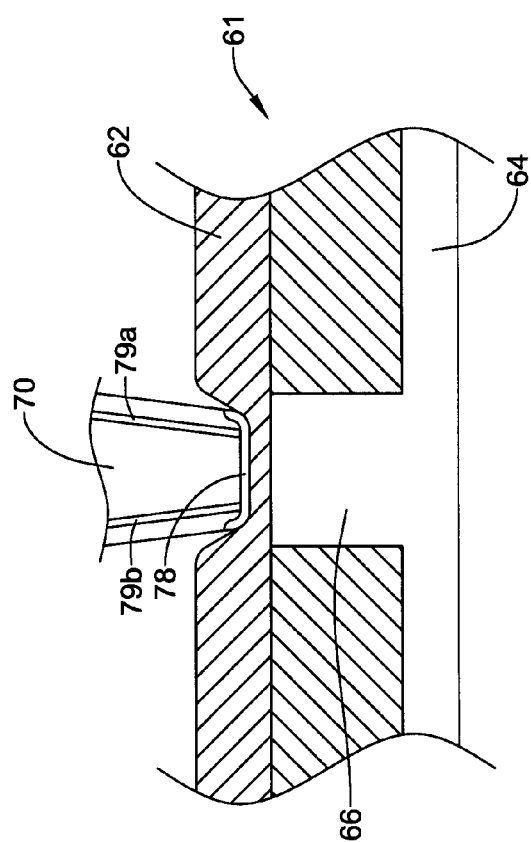
FIG. 6 is a schematic partial cross-sectional side view of yet another illustrative instrument/cartridge interface.

FIG. 6 is a schematic partial cross-sectional side view of yet another illustrative instrument/cartridge interface. This illustrative embodiment is similar to FIG. 5, except that the plunger 70 includes a resilient and/or flexible membrane 78 that can be expanded (e.g. inflated) via fluid pressure to displace the membrane 62 into the storage cavity 66, which in turn, induces a flow in the flow channel 64 of the cartridge 61. More specifically, the plunger 70 may have a first end that is attached to the instrument and a second end that is positioned adjacent the membrane 62 of the cartridge 61. One or more flow channel 79a and 79b may be provided in the axial direction of the plunger 70. The one or more flow channel 79a and 79b may form a pressure conducting path between a pressure source in the instrument and a cavity behind the resilient and/or flexible membrane 78. The shaft 70 may be coupled to a controller that controls the movement of the shaft 70 (up/down) and/or the flow of fluid (gas or liquid) through the one or more flow channel 79a and 79b shaft 70 to the cavity near the shaft tip.

During use, the cartridge 61 may first be positioned in an instrument. In some cases, the instrument may align the shaft 70 with the storage cavity 66 of the cartridge 61. Next, the instrument may move the shaft 70 in contact with the membrane 62, but not yet displacing the membrane 62, if desired. The instrument may then inflate the cavity behind the resilient and/or flexible membrane 78 of the shaft 70, which displaces the membrane 62 into the storage cavity 66, and induces a flow in the flow channel 64 of the cartridge 61. The instrument may then deflate the cavity behind the resilient and/or flexible membrane 78, and withdraw the shaft 70. In some cases, the inflation of the cavity behind the resilient and/or flexible membrane 78 may be made in a pulsing manner or a steady manner. More generally, it is contemplated that the instrument may control the inflation of the cavity behind the resilient and/or flexible membrane 78 at a rate profile that induces a desired flow rate in the flow channel 64 of the cartridge 61. The illustrative process may be automated or under manual control, depending on the application.

Figure 7:
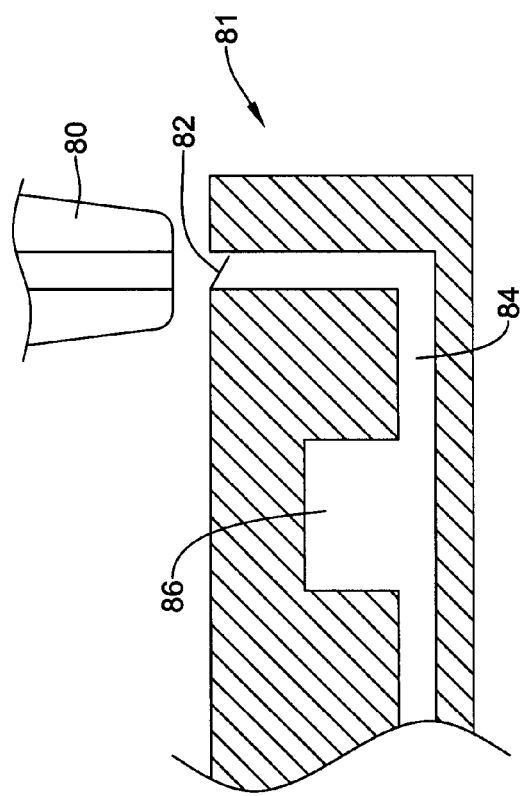
FIG. 7 is a schematic partial cross-sectional side view of another illustrative instrument/cartridge interface.

FIG. 7 is a schematic partial cross-sectional side view of another illustrative instrument/cartridge interface. The illustrative embodiment includes an instrument that has a nozzle 80 for providing a desired flow rate to a flow channel 84 of a cartridge 81. The nozzle 80 may be fluidly coupled to a pressure source (not shown) to provide a pressurized (positive or negative) fluid (gas or liquid) to the nozzle 80. The pressure source may be a pneumatic pump, a compressed gas source, or any other suitable pressure source, as desired.

The nozzle 80 may have a first end attached to the instrument and a second end adapted to engage the cartridge 81. The cartridge 81 may have a flow channel 84 with a flow channel opening at one end. In some cases, there may be a storage cavity 86 fluidly coupled to the flow channel 84 for storing a volume of fluid, such as a sample fluid (e.g. blood). In some cases, the flow channel opening may have a one-way valve 82. The one-way valve 82 may have characteristics that allow fluid or gas to pass through in one direction, but prohibit or substantially prohibit gas or fluid to pass through in the other direction. In some cases, the valve 82 may be configured to prevent the backflow of fluid and/or gas from the cartridge 81, which in some cases, may help reduce the risk of contamination of the instrument or surrounding space.

In some cases, the illustrative nozzle 80 may include a gasket or seal at the second end adjacent the cartridge 81. In addition, or alternatively, the cartridge 81 may include a gasket or seal around the flow channel opening of the cartridge 81. The gasket or seal may help provide a leak-free interface between the nozzle 80 and the cartridge 81. In some cases, the seal may be airtight so that no air or fluid may leak out. The seal may also help reduce contamination by preventing fluid from leaking out of the interface.

To induce a flow in the sample fluid, the cartridge 81 may be inserted and mounted in the instrument (see, for example, FIG. 1). In some cases, the opening in the cartridge 81 may then be aligned with the opening in the nozzle 80. In other cases, the mounting of the cartridge 81 in the instrument automatically ensures that the opening in the cartridge 81 is sufficiently aligned with the opening in the nozzle 80. The nozzle 80 may then be brought into engagement with the cartridge 81 to provide a leak-free interface therebetween. The nozzle 80 may be moved down to the cartridge 81 in an automated or manual manner. For example, a motor or the like may be used to move the nozzle 80 into engagement with the cartridge 81. Alternatively, a user may manually move the nozzle 80 into engagement with the cartridge 81, such as by closing a cover of the instrument (see, for example, FIG. 1).

Once positioned and sealed, pressure may be applied by the instrument into the opening of the cartridge and into the flow channel 84. The pressure may be applied by, for example, pumping fluid or gas though the nozzle 80 and into the flow channel 84. The fluid or gas pumped into the flow channel 84 may displace the fluid in the flow channel 84 and induce a flow therein. In some cases, the fluid or gas pumped into the flow channel 84 may displace a sample fluid (e.g. blood) contained in storage cavity 86.

In some embodiments, a movable stopper or the like (not shown) may be provided in the flow channel 84. The fluid or gas pumped into the flow channel 84 through the nozzle 80 may be on an upstream side of the stopper, and the fluid or gas already in the flow channel 84 (e.g. sample fluid) may be on a downstream side of the stopper. The fluid or gas that is pumped into the flow channel 84 through the nozzle 80 may move the stopper along the flow channel, thereby inducing a flow of the fluid or gas already in the flow channel 84. The stopper may separate the fluid or gas pumped into the flow channel 84 through the nozzle 80 from the fluid or gas already in the flow channel 84. This may help prevent the fluid or gas pumped into the flow channel 84 through the nozzle 80 from mixing with the fluid or gas already in the flow channel 84, when desired.

Figure 8:
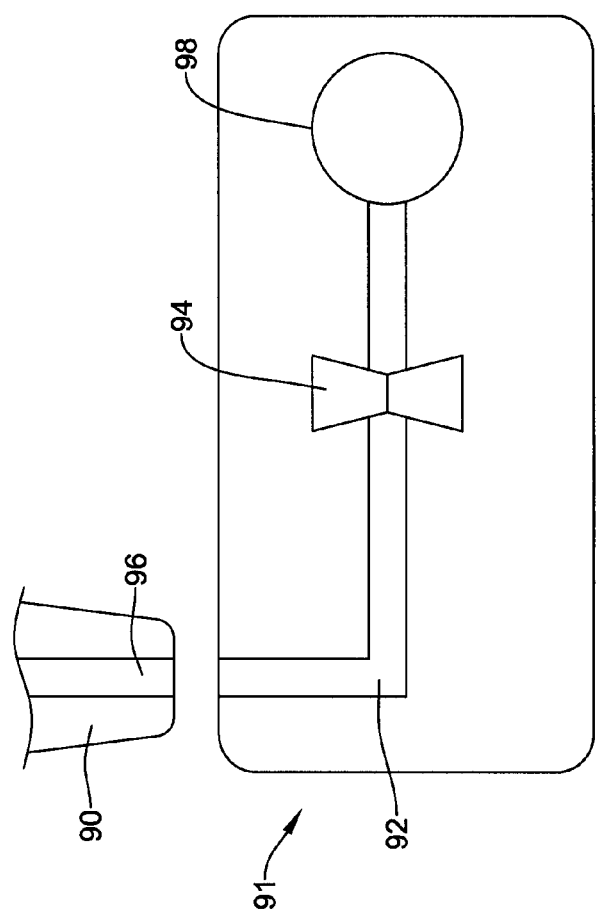
FIG. 8 is a schematic partial cross-sectional side view of an illustrative embodiment for determining a flow rate on a cartridge.

FIG. 8 is a schematic partial cross-sectional side view of an illustrative embodiment for determining a flow rate on a cartridge. The illustrative embodiment includes a nozzle 90 and a cartridge 91, similar to that described above with respect to FIG. 7. In this embodiment, the cartridge 91 may have a flow channel 92 with at least one opening that is adapted to be in fluid communication with the opening 96 of the nozzle 90. In some cases, a restriction 94 may be provided in the flow channel 92 that allows a known flow rate of fluid to pass through the flow channel 92 for a given input pressure provided by nozzle 90. The restriction 94 may be the flow channel 92 itself, or may be a separate feature such as a reduced cross-section section of the flow channel 92.

To determine the flow rate of the fluid through the flow channel 92, the pressure on both sides of the restriction 94 may be sensed. The pressure on the nozzle 90 side of the restriction 94 may be sensed by, for example, a pressure sensor or the like in the instrument itself. The pressure on the downstream side of the restriction 94 may be measured using a pressure sensor on the cartridge. Alternatively, a pressure tap 98 may be provided downstream of the restriction. The pressure tap 98 may include an interface with the instrument, and the instrument may include a pressure sensor to determine the pressure via the pressure tap 98. The interface may include any type of instrument/cartridge interface, including those discussed herein. It is contemplated that, under some circumstances, multiple pressure taps may be used, as desired.

Figure 9:
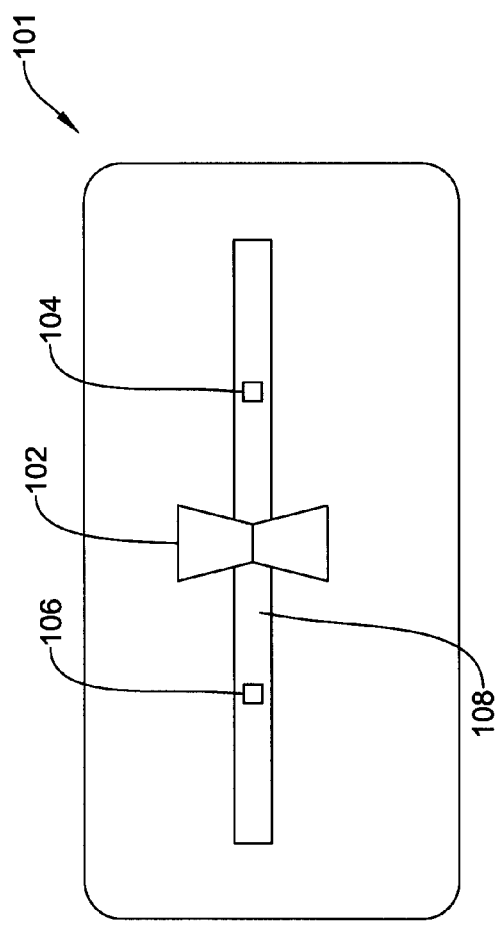
FIG. 9 is a schematic partial cross-sectional side view of another illustrative embodiment for determining a flow rate on a cartridge.

FIG. 9 is a schematic partial cross-sectional side view of another illustrative embodiment for determining a flow rate on a cartridge. This illustrative embodiment is similar to that shown and described with reference to FIG. 8, except two pressure taps 104 and 106 are provided on the cartridge 101, one on each side of a restriction 102. The pressure taps 104 and 106 may have an interface with the instrument, similar to that of FIG. 8. With the two known pressures, the flow rate of the fluid may be determined.

Figure 10:
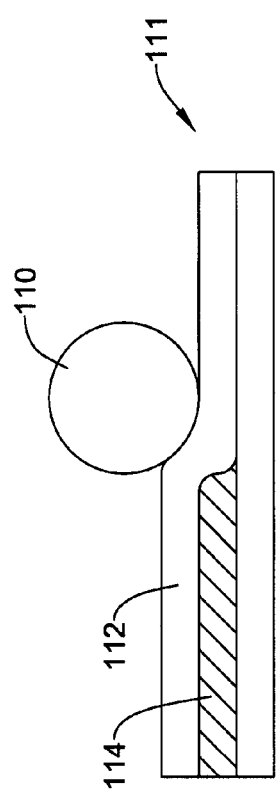
FIG. 10 is a schematic partial cross-sectional side view of an illustrative fluidic analyzer that includes a cartridge with a collapsible flow channel and an instrument with a roller for controllably collapsing the flow channel.

FIG. 10 is a schematic partial cross-sectional side view of an illustrative fluidic analyzer that includes a cartridge 111 with a collapsible flow channel 114 and an instrument with a roller 110 for controllably collapsing the flow channel 114. In the illustrative embodiment, the cartridge 111 includes a flow channel 114 defined by flow channel 114 walls. At least one of the flow channel 114 wall may include, at least in part, a collapsible membrane 112. In some cases, the collapsible membrane 112 may define at least a portion of an outer wall of the flow channel 114. Additionally, in some cases, the other walls of the flow channel 114 may be rigid. The illustrative membrane 112 may be an elastomer or any other flexible material, as desired. Alternatively, the illustrative membrane 112 may be a fairly rigid material that can be collapsed while still maintaining a fluid tight seal about the flow channel 114.

The instrument may include a roller 110 for applying a pressure to the collapsible membrane 112 of the cartridge 111 after it is mounted in the instrument. In one case, the roller 110 may apply a force to the collapsible membrane 112, collapsing the flow channel 114 and continue to roll along the membrane 112, collapsing more of the flow channel 114. In another embodiment, the roller 110 may include multiple shafts that extend toward the cartridge 111 from the instrument. The shafts engage the collapsible membrane 112 over time, applying a force in a sequence where a first shaft on one end extends and collapses the membrane 112, then a next adjacent shaft collapses the membrane 112, and so on, until all the shafts are extended and thus, the flow channel 114 is completely collapsed. More generally, it is contemplated that the roller 110 may be any suitable device 110 for applying a force to the collapsible membrane 112, as desired. It is also contemplated that the force applied by the roller 110 may be a steady force, a rolling force, a pulsing force, or any other suitable method, as desired. Furthermore, the roller 110 may be coupled to a controller for automated control of the roller 110, or alternatively, it is contemplated that the roller 110 may be manually controlled. In the automated situation, the roller 110 may be coupled to a motor or the like, which is controlled by a controller of the instrument.

During use, the cartridge 111 may first be inserted and mounted in the instrument so that the roller 110 is aligned with the collapsible membrane 112. Next, the roller 110 may be positioned adjacent the membrane 112. When ready to create a flow in the flow channel 114, the roller 110 may be activated to apply a force sufficient to collapse part of the collapsible membrane 112. The roller 110 may continue to apply the force along the length of the flow channel 114 to induce a sustained flow in the flow channel 114. The flow rate of the sample fluid may be determined by the cross-sectional area of the flow channel 114 along with the force and speed of the roller 110.

If the collapsible membrane 112 is too flexible, the force that is applied to one portion of the collapsible membrane 112 may cause the fluid in the flow channel 114 to create a force on another portion of the membrane 112, which might cause the collapsible membrane 112 to bulge out or expand to some degree. This may create a non-linearity in the position of the roller 110 and the actual flow induced in the flow channel 114. This non-linearity may be compensated for by calibrating the instrument.

Alternatively, and in some cases, the collapsible membrane 112 may be adapted to not bulge or deform outward when another part of the collapsible membrane is collapsed. For example, the collapsible membrane 112 may be made from a relatively rigid material that resists such bulging. Alternatively, or in addition, another object may be added above the collapsible membrane 112 to help prevent such deformation. In the case when the roller 110 has multiple shafts, all the shafts may be lowered to at or near the collapsible membrane before applying any force to the first shaft, so that it may prevent or substantially prevent any unwanted outward deformation of the membrane 112.

Figure 11:
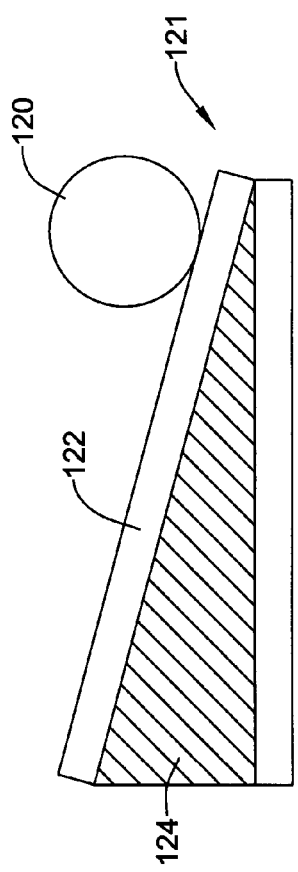
FIG. 11 is a schematic partial cross-sectional side view of another illustrative fluidic analyzer that has a cartridge with a collapsible flow channel and an instrument with a roller for controllably collapsing the flow channel.

FIG. 11 is a schematic partial cross-sectional side view of another illustrative fluidic analyzer that has a cartridge with a collapsible flow channel and an instrument with a roller for controllably collapsing the flow channel. In this illustrative embodiment, the instrument may include a roller 120 that is adapted to apply a force to the cartridge 121, similar to that shown and described with reference to FIG. 10. The cartridge 121 may include a flow channel 124 defined by flow channel 124 walls, including a top wall and a bottom wall. In one embodiment, the flow channel 124 may be collapsible by having a first end that is hinged so that the top wall and the bottom wall of the flow channel 124 form a pivot point, as illustrated. When a force is applied to the top surface of the flow channel 124, the hinge may allow the top surface to collapse toward the bottom surface, squeezing the fluid down the flow channel 124. In some cases, the top surface of the flow channel 124 may have a rigid structure surrounded by a flexible membrane 122, such as an elastic membrane 122, so that when exposed to a force, the membrane 122 allows the top surface to come into contact with the bottom surface. More generally, it is contemplated that any suitable method of collapsing the flow channel 124 may be used, as desired.

Figure 12:
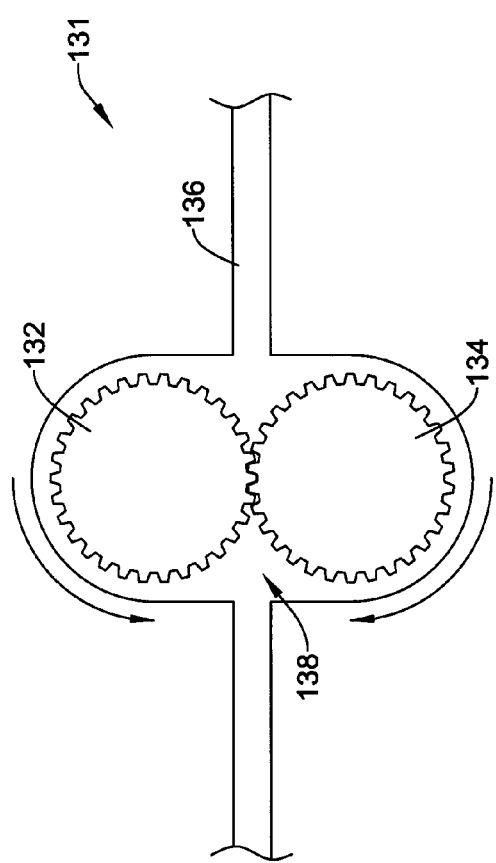
FIG. 12 is a schematic top view of a cartridge that includes a number of gears for inducing a flow in a flow channel of the cartridge.

FIG. 12 is a schematic top view of a cartridge that includes a number of gears for inducing a flow in a flow channel of the cartridge. The illustrative embodiment includes a cartridge 131 having a flow channel 136 with a chamber 138. The chamber 138 includes a number of gears 132 and 134. The gears 132 and 134 may form a pump that is capable of pumping fluid to induce a flow in the flow channel 136. In some cases, each gear 132, 134 may have multiple paddle-like structures around the periphery of the gear. The paddle-like structures may help push the fluid through the chamber 138. As illustrated, the two gears 132 and 134 may rotate in opposite directions of each other and may either push the sample fluid around the outside of the chamber 138 or between the gears 132 and 134. More generally, it is contemplated that one, two, three, or any number of gears 132 and 134 may be used, as desired, to create the desired flow.

In some cases, the gears 132 and 134 may be driven by a motor and a shaft. In other cases, the gears 132 and 134 may be driven by electrical or magnetic fields. More generally, it is contemplated that the gears 132 and 134 may be driven by any suitable method.

In the illustrative embodiment, the instrument may include at least part of the driving mechanism for the gears 132 and 134. For example, the instrument may include a motor and a shaft, wherein the shaft interfaces with one or more of the gears 132 and 134. Alternatively, the gears 132 and 134 may include a ferrous material or even be magnetized, and the instrument may provide a rotating magnetic field that drives the gears 132 and 134. The driving mechanism of the instrument may be controlled by a controller. The controller may control the operation of the gears 132 and 134, such as, for example, the starting and stopping of the gears 132 and 134, the speed of rotation of the gears 132 and 134, the rotational direction of the gears 132 and 134, and/or any other parameters, as desired.

FIG. 13 is a schematic view of an illustrative fluidic analyzer that includes an instrument with a detector for determining the flow rate and/or current position of a fluid in a flow channel of a cartridge. The illustrative embodiment includes a cartridge 141 having a flow channel 140. A detector 142 may be provided in the instrument. In one embodiment, the detector 142 may be mounted in the instrument adjacent the flow channel 140 of the cartridge 141. The detector 142 may detect the presence or certain characteristics of the fluid, either optically, electrically, magnetically, or by any other suitable method. In some cases, such as for optical detection, the cartridge 141 may provide a window for the detector 142 to view the fluid in the flow channel 140. It is contemplated that the detector 142 may be coupled to a controller for activating and deactivating the detector 142, and/or for receiving data from the detector 142.

In some cases, and to measure the flow rate of the sample fluid 144 in the cartridge 141, there may be another fluid, such as a pusher fluid 146, that pushes the sample fluid 144 through the cartridge 141. The pusher fluid 146 may be provided to the cartridge 141 by any method previously discussed or any other suitable method, as desired. Additionally, the pusher fluid 146 may include some detectable characteristics to be measured by the detector 142, such as, for example, particles that can be detected either optically, electrically, or magnetically. Thus, to determine the flow rate of the sample fluid 144, the flow rate of the pusher fluid 146 may be detected and determined.

A similar approach may be used to determine when a fluid reaches a point along a flow channel. That is, the detector 142 may be positioned adjacent a location along a flow channel, and the detector 142 may detect the presence of a fluid at the location, either optically, electrically, or magnetically, as desired. This may be used to, for example, detect when a sample fluid such as blood has sufficiently filled a sample fluid input channel, when a sheath or lysing fluid has reached a certain point in a fluidic circuit on the cartridge 141, or for any other suitable purpose, as desired.

FIGS. 14A-14B are schematic views of an illustrative fluidic analyzer that includes an instrument with two (or more) detectors for determining the flow rate and/or current position of a fluid in a flow channel of a cartridge. The illustrative embodiment includes two detectors 152 and 154 attached to an instrument. A cartridge 151 is also provided that includes a flow channel 150. Similar to FIG. 13, the detectors 152 and 154 may detect the presence and/or flow rate of the fluid in the flow channel 150 either optically, electrically, magnetically, or by any other suitable method, as desired. In some cases, the cartridge 151 may have two or more windows for the flow channel 150 to view the fluid in the flow channel 150. The two or more sensor may be provided at a known distance apart from each other. Each sensor may be coupled to a controller to receive and/or transmit data to and from the detectors 152 and 154, as desired.

The fluid flow rate through the flow channel 150 may be determined by, for example, providing a flow down the flow channel 156. In some cases, the flow may be provided by pushing a fluid 158 with a gas 156, such as, for example, air. In the illustrative embodiment, the gas 156 or air may be used to push the fluid so that the end of the sample fluid 158 may be easy to detect, but this is not required. The two or more detectors 152 and 154 may used to determine the flow rate of the fluid 158 by, for example, detecting when all or substantially all of the sample fluid 158 passes by each detector. A controller may determines the time lapse for the fluid 158 to pass by each detector 152 and 154, and knowing the distance between the detectors 152 and 154, determine the flow rate of the fluid 158. The illustrative point in time when the first detector 152 detects the end of the sample fluid 158 is illustrated in FIG. 14A. The illustrative point in time when the second detector 154 detects the end of the sample fluid 158 is illustrated in FIG. 14B. Alternatively, or in addition, the first and second detectors 152 and 154 may be used to detect when a sample fluid 158 first arrives to determine flow rate. In yet another embodiment, the first and second detectors 152 and 154 may be used to detect some other characteristic of the fluid, such as temperature, thermal conductivity or the like. A thermal pulse may be created in the fluid, which can then be detected by the detectors. Resistivity and/or other characteristics of the fluid may also be detected by detectors 152 and 154. Also, the fluid may contain particles, such as beads or the like, that can be detected optically, electrically, or magnetically, to help determine the flow rate of the fluid. It is contemplated that more than two sensors, or only one sensor, can be used, depending on the application.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respect, only illustrative. Changes may be made in details, particularly in matters of shape, size, and arrangement of parts without exceeding the scope of the invention. The invention's scope is, of course, defined in the language in which the appended claims are expressed.

What is claimed is:

1. A fluidic analyzer, comprising:
   a flow channel for transporting a fluid;
   one or more sensors, the one or more sensors positioned relative to the flow channel such that the one or more sensors sense one or more properties of the fluid being transported down the flow channel other than fluid velocity; and
   a controller coupled to the one or more sensors, the controller determining if the fluid that is being transported down the flow channel is of a desired fluid type based on the one or more properties sensed by the one or more sensors, wherein the controller issues an error and halts operation of a fluidic analysis if the fluid that is being transported down the flow channel is not of the desired fluid type.

2. The fluidic analyzer of claim 1 wherein at least one of the one or more sensors is a thermal conductivity sensor.

3. The fluidic analyzer of claim 1 wherein at least one of the one or more sensors is a specific heat sensor.

4. The fluidic analyzer of claim 1 wherein at least one of the one or more sensors is an electrical resistivity sensor.

5. The fluidic analyzer of claim 1 wherein the one or more sensors include a thermal conductivity sensor and a specific heat sensor.

6. The fluidic analyzer of claim 5 further comprising at least one flow rate sensor.

7. The fluidic analyzer of claim 6 wherein the at least one flow rate sensor include a thermal anemometer type flow sensor.

8. The fluidic analyzer of claim 1 wherein the flow channel is part of a disposable fluidic cartridge, and the controller is part of an instrument, wherein the instrument removably receives the disposable fluidic cartridge.

9. The fluidic analyzer of claim 8 wherein at least one of the one or more sensors is part of the disposable fluidic cartridge.

10. The fluidic analyzer of claim 8 wherein at least one of the one or more sensors is part of the instrument that removably receives the disposable fluidic cartridge.

11. A fluidic analyzer, comprising:
    a disposable fluidic cartridge having a flow channel for transporting a fluid;
    an instrument that removably receives the disposable fluidic cartridge, the instrument including a controller; and
    the disposable fluidic cartridge including one or more sensors positioned relative to the flow channel such that the one or more sensors sense one or more properties of the fluid being transported down the flow channel, wherein the one or more properties include at least one of thermal conductivity, specific heat and electrical resistivity the one or more sensors being in communication with the controller of the instrument, wherein the controller in conjunction with the one or more sensors, determines if the fluid being transported down the flow channel is of a desired fluid type based on the one or more properties sensed by the one or more sensors, and issues an error if the fluid that is being transported down the flow channel is not of the desired fluid type.

12. The fluidic analyzer of claim 11 wherein the controller halts operation of a fluidic analysis if the fluid that is being transported down the flow channel is not of the desired fluid type.

13. The fluidic analyzer of claim 11 wherein at least one of the one or more sensors is a thermal anemometer type sensor.

14. The fluidic analyzer of claim 11 further comprising at least one flow rate sensor.

15. A fluidic analyzer, comprising:
    a disposable fluidic cartridge having a flow channel for transporting a fluid;
    an instrument that receives the disposable fluidic cartridge, the instrument including a controller; and
    the instrument including one or more sensors positioned relative to the flow channel such that the one or more sensors sense one or more properties of the fluid being transported down the flow channel, wherein each of the one or more sensors sense a fluid property other than fluid velocity, the one or more sensors in communication with the controller of the instrument, wherein the controller in conjunction with the one or more sensors determines if the fluid being transported down the flow channel is of a desired fluid type based on the one or more properties sensed by the one or more sensors, and issues an error if the fluid that is being transported down the flow channel is not of the desired fluid type.

16. The fluidic analyzer of claim 15 wherein the controller halts operation of a fluidic analysis if the fluid that is being transported down the flow channel is not of the desired fluid type.

17. The fluidic analyzer of claim 15 further comprising at least one flow rate sensor.

* * * * *